United States Patent
Konishi et al.

(10) Patent No.: US 9,074,323 B2
(45) Date of Patent: Jul. 7, 2015

(54) WET WIPE AND METHOD FOR MANUFACTURING THE SAME

(71) Applicant: UNICHARM CORPORATION, Shikokuchuo-shi, Ehime (JP)

(72) Inventors: Takayoshi Konishi, Kanonji (JP); Toshio Hiraoka, Kanonji (JP); Takahiro Ueda, Kanonji (JP); Ayami Suga, Kanonji (JP); Hiromi Yamada, Kanonji (JP)

(73) Assignee: UNICHARM CORPORATION, Shikokuchuo-Shi, Ehime (JP)

( * ) Notice: Subject to any disclaimer, the term of this patent is extended or adjusted under 35 U.S.C. 154(b) by 0 days.

(21) Appl. No.: 14/348,436

(22) PCT Filed: Sep. 25, 2012

(86) PCT No.: PCT/JP2012/075285
§ 371 (c)(1),
(2) Date: Mar. 28, 2014

(87) PCT Pub. No.: WO2013/047862
PCT Pub. Date: Apr. 4, 2013

(65) Prior Publication Data
US 2014/0246159 A1 Sep. 4, 2014

(30) Foreign Application Priority Data
Sep. 29, 2011 (JP) .................... 2011-215072

(51) Int. Cl.
*D21H 27/02* (2006.01)
*B31F 1/07* (2006.01)
(Continued)

(52) U.S. Cl.
CPC .............. *D21H 27/02* (2013.01); *D04H 1/495* (2013.01); *D21H 27/002* (2013.01); *D04H 1/005* (2013.01)

(58) Field of Classification Search
CPC ... D21H 25/005; D21H 27/002; D21H 27/02; D21H 27/005; D21H 27/007; D21H 23/24; D21H 23/46; D21H 23/50; B31F 1/07; D04H 1/465; D04H 11/08; D04H 3/005; D04H 3/015; D04H 3/153; D04H 1/46; A47K 10/16; A47K 7/00; D21F 11/006; D21F 11/008
USPC ................. 162/109, 115, 117, 141, 149, 158; 428/156; 28/103–105; 424/402
See application file for complete search history.

(56) References Cited

U.S. PATENT DOCUMENTS 6,058,583 A * 5/2000 Takeuchi et al. ................. 28/104
6,187,141 B1 * 2/2001 Takeuchi et al. ............... 162/127
(Continued)

FOREIGN PATENT DOCUMENTS

JP 3461122 B 10/2003
JP 2005-319311 A 11/2005
(Continued)

OTHER PUBLICATIONS

International Search Report issued on Jan. 8, 2013 in International Application No. PCT/JP2012/075285.

*Primary Examiner* — Jose Fortuna
(74) *Attorney, Agent, or Firm* — Lowe Hauptman & Ham, LLP

(57) ABSTRACT

A wet wipe includes a nonwoven fabric impregnated with a liquid. A surface layer in a first surface of the nonwoven fabric has an apparent density of 0.030-0.10 g/cm³ in a dry state. A surface layer in a second surface of the nonwoven fabric has an apparent density of 0.12-0.20 g/cm³ in a dry state. Fibers constituting the nonwoven fabric are raised on at least the first surface.

11 Claims, 7 Drawing Sheets

(51) Int. Cl.
*D04H 1/495* (2012.01)
*D21H 27/00* (2006.01)
*D04H 1/00* (2006.01)

(56) References Cited

U.S. PATENT DOCUMENTS

| | | | | |
|---|---|---|---|---|
| 6,669,878 B2 * | 12/2003 | Yamada et al. | | 264/103 |
| 6,749,718 B2 * | 6/2004 | Takai et al. | | 162/115 |
| 7,210,205 B2 * | 5/2007 | Takeuchi et al. | | 28/104 |
| 7,241,711 B2 * | 7/2007 | Takai et al. | | 442/414 |
| 7,250,382 B2 * | 7/2007 | Takai et al. | | 442/414 |
| 8,673,116 B2 * | 3/2014 | Konishi et al. | | 162/157.7 |
| 8,900,411 B2 * | 12/2014 | Konishi et al. | | 162/115 |
| 2002/0065011 A1 * | 5/2002 | Takeuchi et al. | | 442/336 |
| 2002/0100153 A1 * | 8/2002 | Takai et al. | | 28/104 |
| 2003/0100240 A1 * | 5/2003 | Takai et al. | | 442/408 |
| 2003/0232553 A1 * | 12/2003 | Strandqvist | | 442/59 |
| 2004/0161991 A1 * | 8/2004 | Walton et al. | | 442/327 |
| 2005/0281978 A1 * | 12/2005 | Cabell | | 428/97 |
| 2006/0088697 A1 * | 4/2006 | Manifold et al. | | 428/174 |
| 2008/0008853 A1 * | 1/2008 | Hupp et al. | | 428/85 |
| 2008/0010795 A1 | 1/2008 | Mizutani et al. | | |
| 2010/0063470 A1 * | 3/2010 | Suzuki et al. | | 604/367 |
| 2010/0326612 A1 * | 12/2010 | Hupp et al. | | 162/109 |
| 2011/0104970 A1 * | 5/2011 | Barnholtz et al. | | 442/1 |
| 2011/0152808 A1 * | 6/2011 | Jackson | | 604/367 |
| 2011/0244199 A1 * | 10/2011 | Brennan et al. | | 428/196 |
| 2011/0294388 A1 * | 12/2011 | Konishi et al. | | 442/414 |
| 2014/0014284 A1 * | 1/2014 | Konishi et al. | | 162/115 |
| 2014/0121626 A1 * | 5/2014 | Finn et al. | | 604/384 |
| 2014/0246159 A1 * | 9/2014 | Konishi et al. | | 162/109 |

FOREIGN PATENT DOCUMENTS

| | | | |
|---|---|---|---|
| JP | 2006-022412 A | | 1/2006 |
| JP | 2008-002034 A | | 1/2008 |
| JP | 2009097133 A | * | 5/2009 |
| JP | 2009-131474 A | | 6/2009 |
| WO | WO 2007124521 A1 | * | 11/2007 |
| WO | WO 2011053677 A1 | * | 5/2011 |
| WO | WO 2011053946 A1 | * | 5/2011 |
| WO | WO 2013047862 A1 | * | 4/2013 |

* cited by examiner

WET WIPE AND METHOD FOR MANUFACTURING THE SAME

RELATED APPLICATIONS

The present application is a National Phase of International Application Number PCT/JP2012/075285, filed Sep. 25, 2012, which claims priority to of Application Number 2011-215072, filed Sep. 29, 2011.

TECHNICAL FIELD

The present disclosure relates to wet wipes and to methods for manufacturing the wet wipes.

BACKGROUND ART

Japanese Patent No. 3461122 discloses a method for manufacturing bulky paper, comprising the steps of transporting a fiber sheet having a moisture content of 50-85% by weight to a patterning step including an opening pattern net around a sucker to perform suction in the state of holding the fiber sheet on the above-described opening pattern net, applying a heat quantity of 5 kcal/kg or more to the fiber sheet by spraying steam by a heat quantity applicator simultaneously with or before and after the suction to apply the fiber sheet with a pattern corresponding to the opening pattern net, and then obtaining patterned bulky paper by drying in a drying step.

However, the inventor(s) has recognized that since the bulky paper described in Japanese Patent No. 3461122 is the fiber sheet applied with the pattern corresponding to the opening pattern net by pressing the fiber sheet containing predetermined moisture on the opening pattern net, which is a substrate, by the jet pressure of steam, a shape with concavities and convexities, made by the pattern net might easily be destroyed when rewinding or a slit is made and the bulk is difficult to maintain. Further, since the pressing pattern application is performed by the pressure of vapor, it might be difficult to maintain a shape in a wet state unless a thermoplastic fiber and/or the like are used similarly to the embossment technique. Further, the paper is made to be bulky by pressing the fiber sheet to apply the shape with concavities and convexities; however, since fibers are not moved, its fiber density is equivalent to or partially higher than that of the sheet prior to the application of the shape. Further, the paper is a fiber sheet which is not subjected to fiber entanglement and might require a strong agent and/or the like for maintaining strength. Further, due to the shape of concavities and convexities applied by the pattern net, its use as a wipe reduces a contact area, and therefore, wiping-off properties might deteriorate.

SUMMARY

At least one embodiment of the present invention provides a wet wipe comprising a nonwoven fabric impregnated with a liquid. A surface layer in a first surface of the nonwoven fabric has an apparent density of 0.030-0.10 g/cm³ in an absolutely dry state. A surface layer in a second surface of the nonwoven fabric has an apparent density of 0.12-0.20 g/cm³ in an absolutely dry state. Fibers constituting the nonwoven fabric are raised on at least the first surface.

DESCRIPTION OF EMBODIMENTS

At least one embodiment of the present invention provides a wet wipe comprising a nonwoven fabric impregnated with a liquid. A surface layer in a first surface of the nonwoven fabric has an apparent density of 0.030-0.10 g/cm³ in an absolutely dry state. A surface layer in a second surface of the nonwoven fabric has an apparent density of 0.12-0.20 g/cm³ in an absolutely dry state. Fibers constituting the nonwoven fabric are raised on at least the first surface.

The wet wipe has a high effect of wiping off fouling and enables rough wiping and finishing wiping with one sheet since the apparent densities of the front and back (i.e., first and second) surfaces thereof are different and fibers are raised on at least the surface having the lower apparent density (i.e., the first surface). Further, the wet wipe is bulky and offers soft feeling due to fiber raising, so that it may be used as a wipe for use in humans, where soft texture is desirable, e.g., for wiping the buttocks. Further, chilly feeling can be reduced when the skin is touched since a raised portion has a lower water retentivity than that of a sheet portion.

Some embodiments of the present invention will be described below with reference to the drawings, but the present disclosure is not limited to the descriptions of the drawings.

Figure 1:
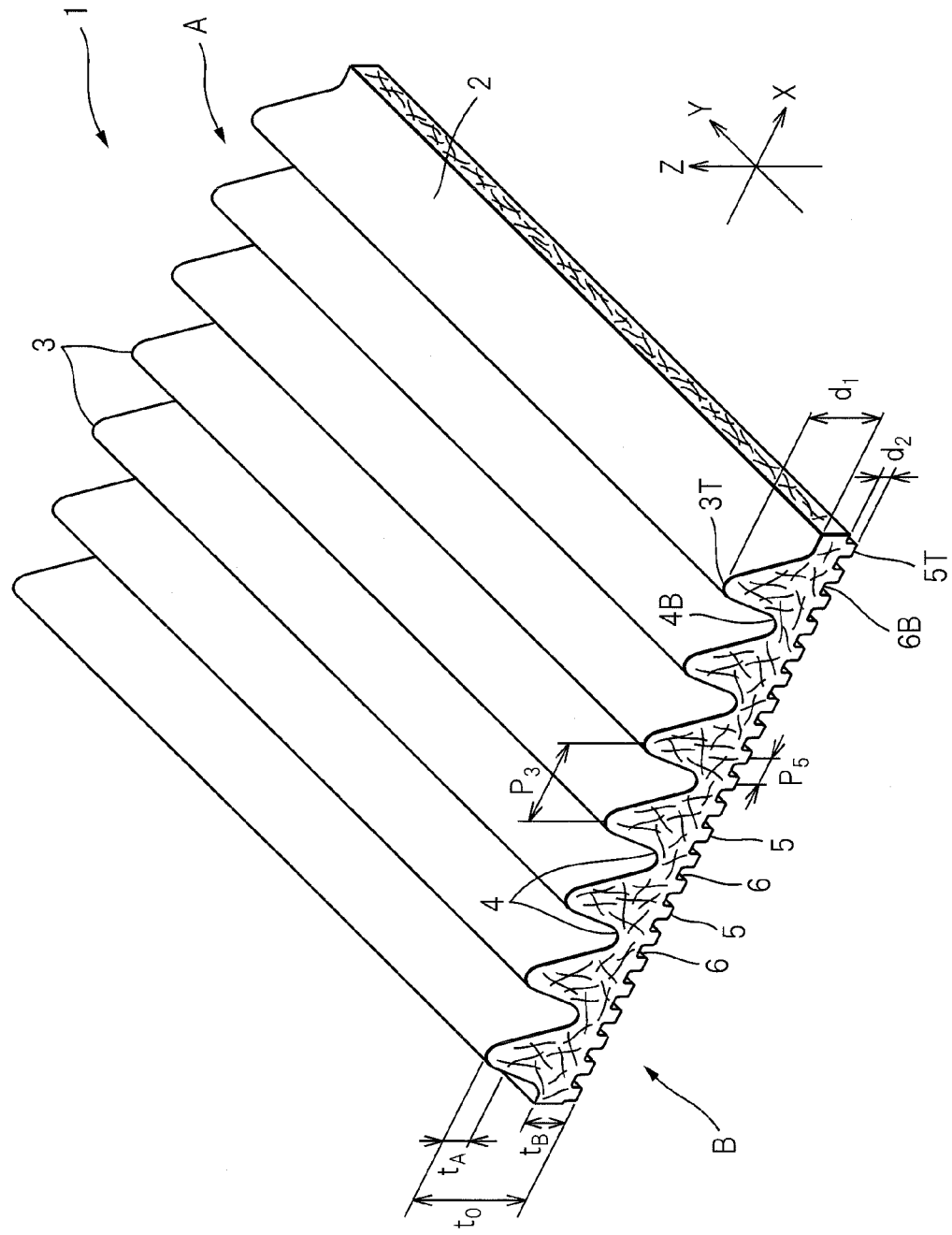
FIG. 1 is a schematic enlarged perspective view of the wet wipe according to at least one embodiment of the present invention.

FIG. 1 is the schematic enlarged perspective view of the wet wipe 1 according to at least one embodiment of the present invention. The wet wipe 1 according to at least one embodiment of the present invention comprises a nonwoven fabric impregnated with a liquid; however, since the liquid is not illustrated in FIG. 1, FIG. 1 is also a schematic enlarged perspective view of the nonwoven fabric 2 constituting the wet wipe.

In the wet wipe 1 according to at least one embodiment of the present invention, a surface layer on the first surface of the nonwoven fabric 2 has an apparent density of 0.030-0.10 g/cm³ in a dry state, while a surface layer in the second surface of the nonwoven fabric has an apparent density of 0.12-0.20 g/cm³ in a dry state. Hereinafter, the first surface in which the surface layer has the apparent density of 0.030-0.10 g/cm³ in the dry state is also referred to as a surface having a lower apparent density, and the second surface in which the surface layer has the apparent density of 0.12-0.20 g/cm³ in the dry state is also referred to as a surface having a higher apparent density. In FIG. 1, the surface having a lower apparent density is represented by A and the surface having a higher apparent density is represented by B. As used herein, a "surface layer" refers to a part from the top of the convexity of a surface to 30% of a thickness of the non-woven fabric. As used herein, a "thickness" of the non-woven fabric refers to a distance $t_0$ between the top (first ridge portion) of the convexity of a first surface and the top (the second ridge portion) of the convexity of a second surface. That is, $t_A=t_B=0.30\ t_0$ holds in FIG. 1, where $t_A$ corresponds to the surface layer in the surface having a lower apparent density and $t_B$ corresponds to the surface layer in the surface having a higher apparent density.

The term "dry state" as stated herein means "absolutely dry state," i.e., a state after leaving at rest in a constant-temperature bath at 105° C. for 1 hour.

The apparent density of a surface layer in a dry state is measured as described below.

The cross section of a nonwoven fabric is macrophotographed at a magnification of 50 times or more by a microscope or the like, the number of fibers per unit area of $t_A$ or $t_B$ in depth×0.5 mm in width is measured, and the weight of the fibers is calculated from the result to calculate the apparent density.

In the wet wipe 1 according to at least one embodiment of the present invention, fibers are raised on at least the surface A having a lower apparent density. As used herein, raising fibers refers to the state in which the density of the fibers constituting a nonwoven fabric is partially decreased. The raised fibers can be formed by blowing weakly entangled fibers together with application of steam. The details of the formation method are described below.

The apparent density of the surface layer in the surface A having a lower apparent density is 0.030-0.10 g/cm³ in a dry state, preferably 0.04-0.09 g/cm³, more preferably 0.05-0.08 g/cm³. The number of fibers on the convexity is excessively decreased to easily cause weakening when the apparent density of the surface layer in the surface A is too low whereas the number of fibers is excessively increased to preclude fouling from entering and to deteriorate wiping-off properties when it is too high.

The apparent density of the surface layer in the surface B having a higher apparent density is 0.12-0.20 g/cm³ in a dry state, preferably 0.13-0.19 g/cm³, more preferably 0.14-0.18 g/cm³. A contact area is reduced to cause roughened wiping, which might not be suitable for finishing wiping, when the apparent density of the surface layer in the surface B is too low whereas it is easy to become paper-like to easily cause hard feeling when it is too high.

In a preferred embodiment of the present invention, the fibers raised on the surface having a lower apparent density form a plurality of first ridges 3 extending in parallel in an elongation direction; and a plurality of first grooves 4 each formed between two adjacent first ridges 3, 3. In contrast, a plurality of second ridges 5 extending in the elongation, and second grooves 6 are formed on the surface B having a higher apparent density.

In a preferred embodiment of the present invention, a distance $d_1$ between the top 3T of the first ridge and the bottom 4B of the first groove is greater than a distance $d_2$ between the top 5T of the second ridge and the bottom 6B of the second groove.

The distance $d_1$ between the top 3T of the first ridge and bottom 4B of the first groove is preferably 0.15-0.60 mm, more preferably 0.17-0.55 mm, further preferably 0.20-0.50 mm. Raised fibers are too short and an effect of taking fouling by entanglement is decreased when the distance $d_1$ is too short whereas maintenance of an applied shape becomes difficult and the amount of fibers falling out is increased when the distance $d_1$ is too long.

The distance $d_2$ between the top 5T of the second ridge and the bottom 6B of the second groove is preferably 0.05-0.10 mm, more preferably 0.06-0.09 mm, further preferably 0.07-0.08 mm. It becomes paper-like to cause hard feeling when the distance $d_2$ is too short whereas a contact area becomes small to deteriorate a finishing wiping effect when the distance $d_2$ is too long.

In a preferred embodiment of the present invention, a spacing $p_3$ between two adjacent first ridges is greater than a spacing $p_5$ between two adjacent second ridges.

The spacing $p_3$ between the two adjacent first ridges is preferably 1.0-3.0 mm, more preferably 1.2-2.5 mm, further preferably 1.5-2.0 mm. The amount of fibers blown together is decreased and $d_1$ is increased to cause difficulty when the spacing $p_3$ is too short whereas fibers, which are blown together from right and left are aggregated to form a convexity, are not aggregated to be unable to form a large convexity when the spacing $p_3$ is too long.

The spacing $p_5$ between the two adjacent second ridges is preferably 0.3-1.0 mm, more preferably 0.4-0.8 mm, further preferably 0.5-0.7 mm. It is difficult to form concavities and convexities when the spacing $p_5$ is too short whereas a portion having weakly entangled fibers is formed to cause great unevenness in sheet strength when the spacing $p_5$ is too long.

The first ridges 3 and the first grooves 4 can be formed by spraying steam and the second ridges 5 and the second grooves 6 can be formed by spraying a stream of water. The details of the formation methods are described below.

Preferably, 30% by weight or more, more preferably 35% by weight or more, further preferably 40% by weight or more, of fibers constituting the nonwoven fabric are absorbable fibers (i.e., fibers that can absorb water). Percent by weight is based on weight in an absolutely dry state. Weight in an absolutely dry state is weight after drying at 105° C. for 1 hour. All the fibers constituting the nonwoven fabric may also be absorbable fibers.

Such absorbable fibers which can be used in various embodiments of the present invention include: wood pulp such as chemical, semichemical, and mechanical pulp from coniferous and broadleaf trees; mercerized and cross-linked pulp prepared by chemical treatment of the wood pulp; non-wood-based fibers from hemp, cotton, and the like; cellulosic fibers such as regenerated fibers such as rayon fibers; and polyvinyl alcohol fibers. The absorbable fiber preferably contains cellulose.

Fibers other than the absorbable fibers include synthetic fibers such as polyethylene, polypropylene, polyester, and polyamide fibers.

The fibers constituting the nonwoven fabric preferably have fiber lengths of 20 mm or less, more preferably 1-20 mm, even more preferably 1-15 mm, further preferably 2-12 mm. Their homogeneous dispersion in water becomes difficult to easily degrade contexture when the fiber lengths are too long. In contrast, a yield is decreased during making paper and hydroentanglement is difficult to easily decrease strength when they are too short.

The wet wipe according to at least one embodiment of the present invention contains a nonwoven fabric impregnated with a liquid, and such liquids with which the nonwoven fabric is impregnated include distilled water and mixed solutions of antiseptic agents such as propylene glycol and paraben.

The wet wipe according to at least one embodiment of the present invention can be manufactured by a method comprising the steps of:

supplying a mixture of fibers with water onto a substrate to form a web containing water on the substrate;

spraying a water stream onto a surface of the web from water stream nozzles placed in the cross direction of the web (i.e., the direction that is perpendicular to the direction of travel of the web) at equal spacings to entangle the fibers;

spraying steam or a mixture of steam with another gas onto an opposite surface of the web from steam nozzles placed in the cross direction of the web at wider spacings than the spacings of the water stream nozzles, to raise the fibers to obtain a nonwoven fabric with the different apparent densities on the front and back (first and second) surfaces; and impregnating the obtained nonwoven fabric with a liquid.

The method for manufacturing the wet wipe according to at least one embodiment of the present invention will be described in detail below.

Figure 2:
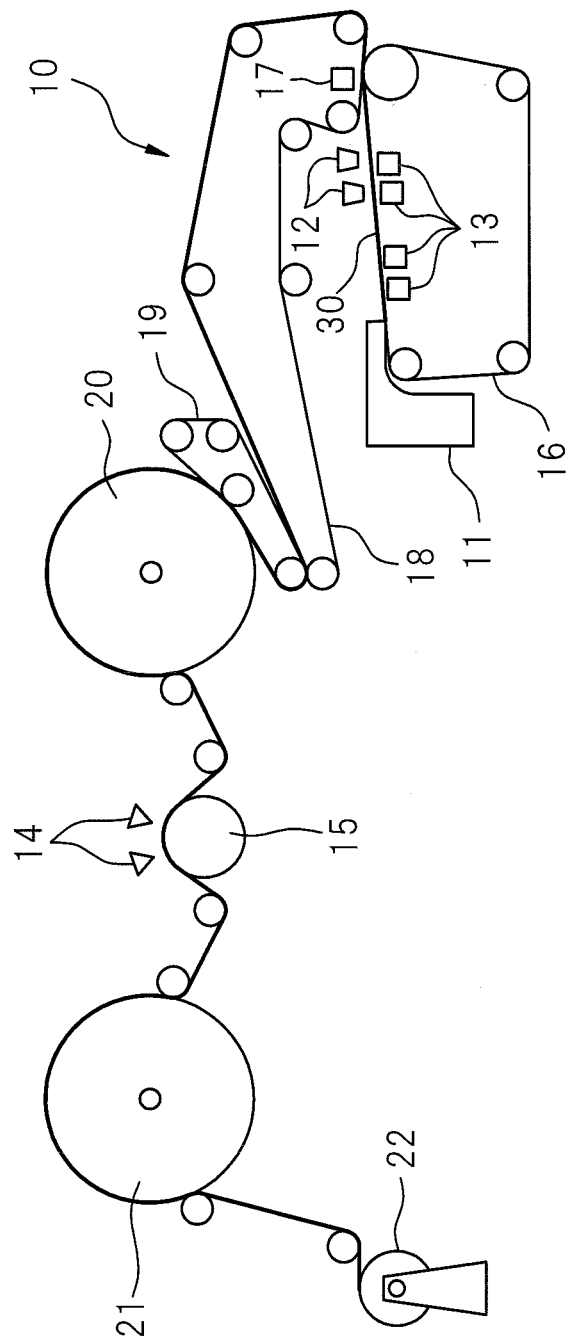
FIG. 2 is a view that illustrates an example of a nonwoven fabric manufacturing apparatus for manufacturing a nonwoven fabric in accordance with at least one embodiment of the present invention.

FIG. 2 is a view that illustrates an example of a nonwoven fabric manufacturing apparatus for manufacturing a nonwoven fabric in accordance with at least one embodiment of the present invention.

First, a mixture of fibers with water is prepared. The mixture of the fibers with the water is supplied onto the substrate of a web formation conveyer 16 by a raw material supply head 11 and accumulated on the substrate. The substrate preferably has such permeability that steam is permeable. For example, a wire mesh, a blanket, or the like may be used in the substrate.

The fibers accumulated on the substrate and containing the water are moderately dehydrated by suction boxes 13 to form a web 30. The web 30 is passed between two water stream nozzles 12 which are placed on the substrate and the two suction boxes 13 which are placed in the positions facing the water stream nozzles 12 across the substrate and collect water jetted from the water stream nozzles 12. At this time, water streams are sprayed on the web 30 from the water stream nozzles 12 to form the second ridges and the second grooves on an upper surface (i.e., the surface closer to the water stream nozzles 12; hereinafter referred to as "B surface").

Figure 3:
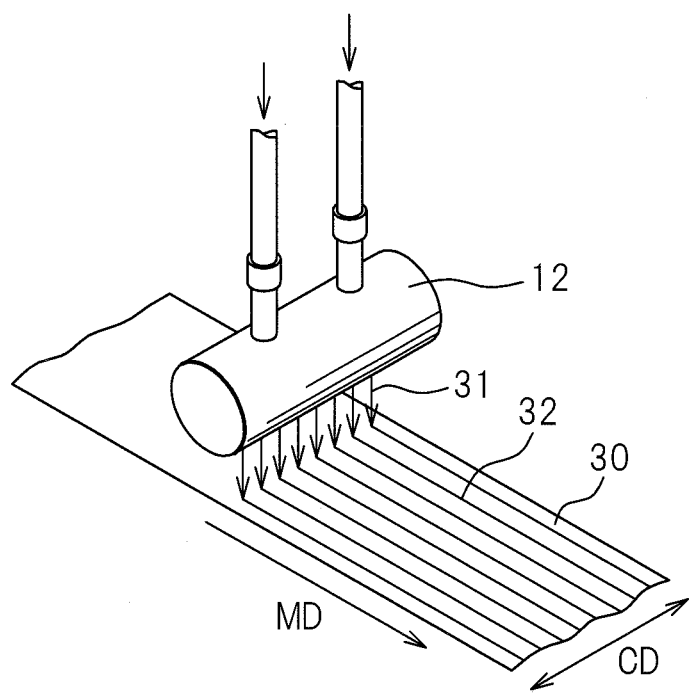
FIG. 3 is a view that illustrates an example of water stream nozzles.

An example of the water stream nozzles 12 is illustrated in FIG. 3. The water stream nozzle 12 blows toward the web 30 a plurality of water streams 31 lined in the cross direction (CD) of the web 30. As a result, a plurality of grooves 32 that are lined in the cross direction of the web 30 and extend in a machine direction (MD) are formed on the upper surface of the web 30. The grooves 32 correspond to the second grooves 6.

Further, when the web 30 receives the water streams, the grooves 32 are formed on the web 30 as mentioned above and the fibers of the web 30 are entangled with each other to increase the strength of the web 30. The principle of entangling the fibers of the web 30 with each other when the web 30 receives the water streams is described referring to FIG. 4, but the principle does not limit the present invention.

Figure 4:
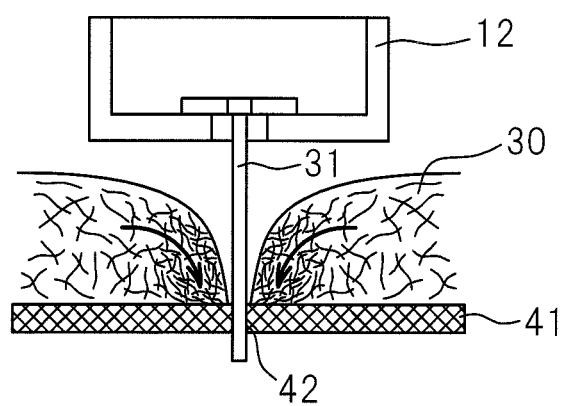
FIG. 4 is a view for explaining the principle of entangling the fibers of a web with each other by water stream spraying.

As illustrated in FIG. 4, when the water stream nozzle 12 jets the water stream 31, the water stream 31 passes through the substrate 41. Thereby, the fibers of the web 30 are drawn mainly in a part 42 where the water stream 31 passes through the substrate 41. As a result, the fibers of the web 30 are gathered towards the part 42 where the water stream 31 passes through the substrate 41, to entangle the fibers with each other.

Even when steam is sprayed on the web 30 in a later step, formation of a hole, breaking, and blowing off are inhibited by entangling the fibers of the web 30 with each other to increase the strength of the web 30. Further, the wet strength of the web 30 can be increased even when no paper strong agent is added to the raw materials of a nonwoven fabric.

The amount of the energy of the water stream is preferably 0.125-1.324 kW/m². The amount of the energy of the water stream is calculated by the following expression:

$$\text{amount of energy (kW/m}^2\text{) of water stream} = 1.63 \times \text{jet pressure (Kg/cm}^2\text{)} \times \text{jet flow rate (m}^3\text{/min)/treatment speed (m/min)/60}$$

wherein jet flow rate (m³/min)=750×total orifice opening area (m²)×jet pressure (Kg/cm²)$^{0.495}$.

The amount of the energy of the water stream is an amount of the energy of the water stream on the surface of the web.

When the amount of the energy of the water stream is too small, the strength of the web 30 may not increase much. On the contrary, when the amount of the energy of the water stream is too large, the web 30 may become too rigid and the web 30 may be prevented from becoming more bulky by high-pressure steam.

The water stream nozzles 12 preferably have bore diameters of 90-150 μm. When the water stream nozzles 12 have bore diameters of less than 90 μm, a problem that the nozzles are easily clogged may occur. Further, when the water stream nozzles 12 have bore diameters of more than 150 μm, treatment efficiency may deteriorate.

The bore pitches (distances between the centers of adjacent bores) of the water stream nozzles 12 are preferably 0.3-1.0 mm. When the bore pitches of the water stream nozzles 12 are less than 0.3 mm, a problem that the withstand pressures of the nozzles are decreased to damage them may occur. Further, when the bore pitches of the water stream nozzles 12 are more than 1.0 mm, a problem that fiber entanglement becomes insufficient may occur.

Figure 5:
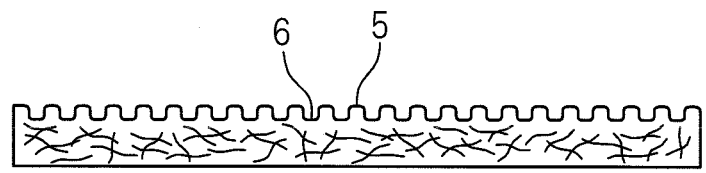
FIG. 5 is a cross-sectional view of a web, on which a water stream is sprayed, in a cross direction.

The cross section of the web 30 in the cross direction after passing between the two water stream nozzles 12 and the two suction boxes 13 is illustrated in FIG. 5. The second ridges 5 and the second grooves 6 are formed on the upper surface of the web 30 by water streams.

Then, the web 30 is transferred to a web transportation conveyer 18 by a suction pickup 17, as illustrated in FIG. 2. Furthermore, the web 30 is transferred to a web transportation conveyer 19 and then transferred to a dryer drum 20. The dryer drum 20 is, e.g., a yankee dryer, and the web 30 is attached to the drum heated to about 120° C. by steam to dry the web 30.

Drying with the dryer drum 20 preferably causes the web 30 to have a moisture content of 10-45%. As used herein, moisture content is the gram of water contained based on the total mass of 100 g of the web containing the water. When the moisture content of the web 30 is too low, hydrogen bonding strength between the fibers of the web 30 is increased to make energy needed for disentangling the fibers of the web 30 by steam as mentioned below very high. In contrast, when the moisture content of the web 30 is too high, energy needed for drying the web 30 to predetermined moisture content or less by steam as described below is made to be very high.

Then, the web 30 is moved onto the mesh-like outer peripheral surface of a suction drum 15 which is cylindrical. When this occurs, steam is sprayed on the web 30 from the steam nozzle 14 placed above the outer peripheral surface of the suction drum 15. Two lines of the steam nozzles 14 are placed in FIG. 2; however, one line of the steam nozzle 14 may be placed or three or more lines may be placed. The surface of the web on which steam is sprayed is the surface opposite to the surface (B surface) on which water streams are sprayed (hereinafter referred to as "A surface"). The suction drum 15 includes a suction apparatus and steams sprayed from the steam nozzles 14 are sucked in the suction apparatus. The first ridges 3 and the first grooves 4 are formed on the A surface of the web 30 by the steams sprayed from the steam nozzles 14.

The steam sprayed from the steam nozzle 14 is high-pressure steam. A steam spraying pressure is preferably 0.3-1.5 MPa, more preferably 0.4-1.2 MPa, further preferably 0.5-1.0 MPa. An effect of blowing fibers together is weak to preclude formation of a convexity when the steam spraying pressure is too low whereas damage to a sheet is excessively increased to easily cause decrease in strength when it is too high.

The steam sprayed from the steam nozzles 14 may also be a mixture with another gas such as air but preferably contains only steam.

Figure 6:
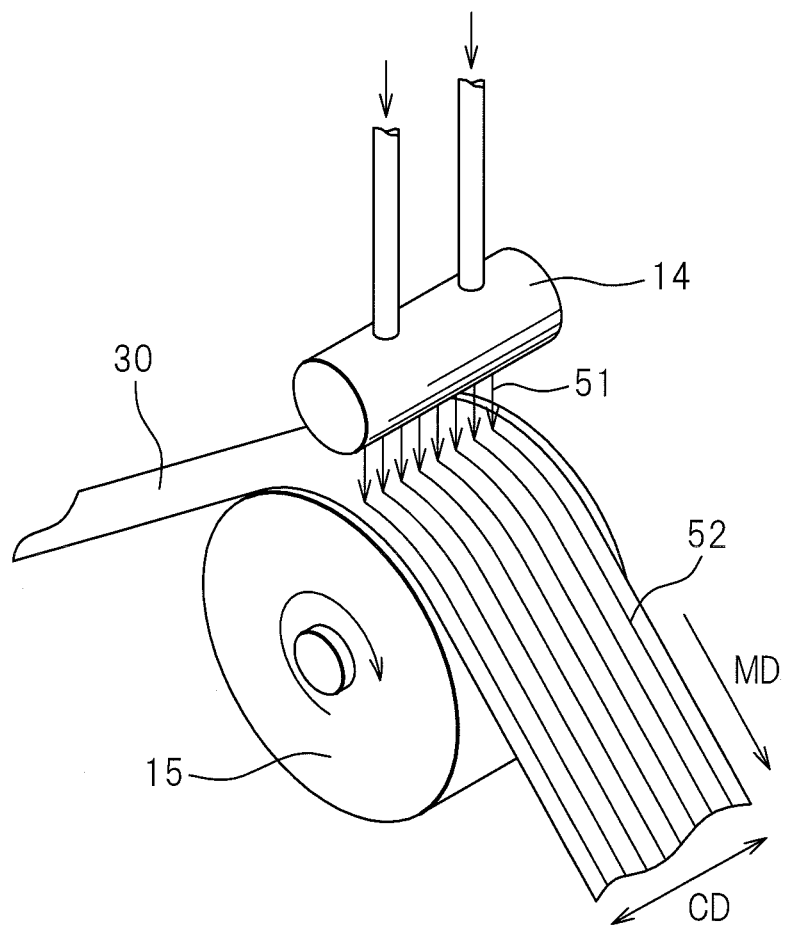
FIG. 6 is a view that illustrates an example of a steam nozzle.

An example of the steam nozzles 14 placed above the suction drum 15 is illustrated in FIG. 6. The steam nozzle 14 sprays toward the web 30 a plurality of steams 51 lined in the cross direction (CD) of the web 30. As a result, a plurality of grooves 52 that are lined in the cross direction of the web 30 and extend in a machine direction (MD) are formed on the A surface of the web 30. The grooves 52 correspond to the first grooves 4.

When the high-pressure steam is jetted to the web 30, the fibers of the web 30 are disentangled and the web 30 becomes more bulky. Thereby, the flexibility of the web 30 rigidified by pressure and water streams during transfer is increased to improve the feeling of the web 30. The principle of disentangling the fibers of the web 30 to make the web 30 more bulky when the web 30 receives steam is described referring to FIG. 7, but the principle does not limit the present invention.

Figure 7:
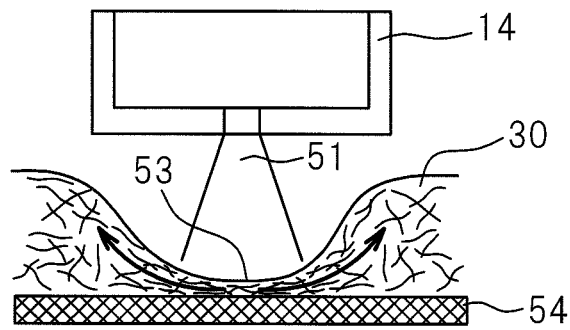
FIG. 7 is a view for explaining the principle of disentangling the fibers of a web by spraying steam to raise the fibers.

As illustrated in FIG. 7, when the steam nozzle 14 sprays the steams 51, the steams 51 hit the mesh-like outer peripheral surface 54 of the suction drum. Most of the steams 51 are rebounded by the outer peripheral surface 54. Thereby, the fibers of the web 30 are rolled up and disentangled. Further, the fibers of the web 30 are pushed aside by the steams 51 to reduce a mass per unit area immediately below the steam nozzle 14 (first grooves). The fibers pushed aside are moved to gather to the cross direction side of the part 53 of the outer peripheral surface 54, hit by the steams 51, the web 30 is made to be more bulky, and the state in which the fibers are raised is formed (first ridges). By high-pressure steam treating of the surface that has relatively weakly entangled fibers and is opposite to the surface subjected to hydroentanglement treatment, they can be disentangled easily in comparison with the hydroentanglement surface, a raised-fiber structure is easily made since fibers are entangled and fixed in a hydroentanglement portion in a lower layer side, and reduction in the strength of the sheet can be minimized since the entanglement portion is not broken.

Since the strength of web 30 is enhanced by the water streams, it is not necessary to place on the web 30 a net for preventing the web 30 from being blown off by the steams 51 when the high-pressure steams 51 are sprayed on the web 30. Accordingly, the efficiency of treatment of the web 30 by the steams 51 is increased. Further, since it is not necessary to place the above-described net, the maintenance of the nonwoven fabric manufacturing apparatus and the cost of manufacturing a nonwoven fabric can be reduced.

The steam sprayed from the steam nozzle 14 is high-pressure steam, of which the steam pressure is preferably 0.3-1.5 MPa. When the pressure of the steam is lower than 0.3 MPa, the web 30 may not be made to be much more bulky by the steam. When the pressure of the steam is higher than 1.5 MPa, a hole may be formed in the web 30 or the web 30 may be broken or blown off.

Suction force at which the suction drum 15 sucks the web 30 by a suction apparatus which sucks the steam sprayed from the steam nozzles 14 and is included in the suction drum 15 is preferably −1 to −12 kPa. When the suction force of the suction drum 15 is lower than −1 kPa, all of the steam cannot be sucked, which results in an explosion. Further, when the suction force of the suction drum 15 is higher than −12 kPa, a problem that there are many fibers falling in the suction may occur.

A distance between the bore of the steam nozzle 14 and the upper surface of the web 30 is preferably 1.0-10 mm. When the distance between the bore of the steam nozzle 14 and the upper surface of the web 30 is shorter than 1.0 mm, a problem that a hole is formed in the web 30 or the web 30 is broken or blown off may occur. Further, when the distance between the bore of the steam nozzle 14 and the upper surface of the web 30 is longer than 10 mm, force for forming the grooves on the surface of the web 30 by the high-pressure steam is dispersed to deteriorate the efficiency of forming the grooves on the surface of the web 30.

The bore diameter of the steam nozzle 14 is preferably larger than the bore diameter of the water stream nozzle 12 and the bore pitch (spacing) of the steam nozzle 14 is preferably larger than the bore pitch (spacing) of the water stream nozzle 12.

The bore diameter of the steam nozzle 14 is preferably 150-600 μm. When the bore diameter of the steam nozzle 14 is too small, energy is insufficient and fibers may not sufficiently be pushed aside. Further, when the bore diameter of the steam nozzle 14 is too large, energy becomes too large and damage to the substrate may be excessive.

The bore pitch (distance between the centers of adjacent bores) of the steam nozzle 14 is preferably 1.0-3.0 mm. When the bore pitch of the steam nozzle 14 is too short, a problem that the withstand pressure of the nozzle is decreased to cause the fear of breakage may occur. Further, when the bore pitch of the steam nozzle 14 is too long, improving flexibility is deteriorated due to insufficient treatment may occur.

The temperature of the steam is preferably higher than the temperature of the dryer drum 20 in order to maximumly prevent the moisture content of the web 30 sprayed with steam from being higher than the moisture content of the web 30 prior to being sprayed with steam. For example, the temperature of the steam is preferably 130-220° C. Thereby, drying of the web 30 proceeds even when steam is sprayed on the web 30, so that the web 30 is made to be more bulky and dried. Since hydrogen bond between the fibers of the web 30 is increased when the web 30 is dried, the strength of the web 30 is increased to inhibit the increased bulk of the web 30 from being broken. Further, the increase in the strength of the web 30 prevents a hole from being formed in the web 30 and the web 30 from being cut by spraying steam.

The moisture content of the web 30 after being sprayed with steam is preferably 45% or less, more preferably 40% or less. When the moisture content of the web 30 after being sprayed with steam is higher than 45%, the moisture content of the web 30 may not be made to be 5% or less by drying with the dryer drum as described below. In this case, further additional drying is necessary and the efficiency of manufacturing a nonwoven fabric deteriorates.

Then, the web is transferred to a dryer drum 21 which is different from the dryer drum 20 as illustrated in FIG. 2. The dryer drum 21 is also, for example, a yankee dryer and the web 30 is attached to the drum heated to about 150° C. by steam to dry the web 30. It is preferred that the web 30 passed through the dryer drum 21 is sufficiently dried, and specifically, the moisture content of the web 30 passed through the dryer drum 21 is preferably 5% or less.

The dried web 30 is wound up as a nonwoven fabric by a wind-up machine 22.

A wet wipe is obtained by impregnating the manufactured nonwoven fabric with a liquid. Methods for impregnation of liquids include, without limitation, for example, spray impregnation and pad impregnation.

In the high-pressure hydroentanglement treatment, fibers are entangled and a nonwoven fabric is tightened (increasing density) to increase the strength of the nonwoven fabric.

In the high-pressure steam treatment, fibers are disentangled (decreasing density) to make a nonwoven fabric more bulky. In this case, since the amount of energy is higher in the high-pressure water stream treatment, only a part of the nonwoven fabric is disentangled and the fibers can be raised without being scattered in the high-pressure steam treatment.

When the high-pressure steam spraying treatment of the surface side subjected to the high-pressure water stream spraying treatment is performed, energy for water stream spraying is higher and it is difficult to disentangle fibers. Since it is also a part where fibers are strongly entangled and web strength is developed, the strength is significantly decreased when the fibers on the hydroentanglement surface side are disentangled. Thus, in accordance with at least one embodiment of the present invention, a shape with concavities and convexities in the state of raising fibers and by steam-sprayed line marks is applied by performing the high-pressure steam spraying treatment of the surface side which is opposite to the surface subjected to the high-pressure water stream spraying treatment and has the relatively weakly entangled fibers.

Fouling can be removed by the wet wipe according to at least one embodiment of the present invention as described below.

First, when fouling, solid fouling is taken and removed by entanglement on a surface A on which fibers are raised (surface on which large ridges and grooves are formed). The solid fouling is taken and removed by entanglement by the raised portions (first ridges) of the surface A on which the fibers are raised and steam-sprayed line marks (first grooves) made by spraying steam. Then, finishing wiping of microfouling such as residues after wiping can be performed on an opposite surface B having a high apparent density (surface on which small ridges and grooves are formed). The microfouling is scraped away by water stream-sprayed line marks (second grooves).

By changing the front and back structure of one nonwoven fabric, a surface excellent in rough fouling wiping and a surface excellent in microfouling wiping can be placed and a wipe that enables rough wiping and finishing wiping with one wipe can be realized. Further, since the rough wiping surface employs not only concavities and convexities but also raised fibers, the effect of taking fouling by entanglement is higher than that in the case of only concavities and convexities.

EXAMPLES

Example 1

A nonwoven fabric was produced using the nonwoven fabric manufacturing apparatus 10 of FIG. 2, as described below.

A raw material for a nonwoven fabric, containing 70 mass % of bleached softwood kraft pulp (NBKP) (Canadian Standard Freeness (CSF) 700 cc) and 30 mass % of rayon having a fineness of 1.1 dtex and a fiber length of 7 mm (Corona manufactured by Daiwabo Rayon Co., Ltd.), was prepared. The raw material for a nonwoven fabric was supplied onto the substrate (OS80 manufactured by Nippon Filcon Co., Ltd.) of a web formation conveyer using the raw material supply head 11 and the suction box was used to dehydrate the raw material for a nonwoven fabric to form a web. The web in this case had a mass per unit area of 50 g/m$^2$. Then, high-pressure water streams were sprayed on the web using two high-pressure water stream nozzles. The bore diameters of the high-pressure water stream nozzles were 92 μm, the bore pitch of the high-pressure water stream nozzles was 0.5 mm, the amount of the energy of the high-pressure water streams sprayed on the web using the two high-pressure water stream nozzles was 0.284 kW/m$^2$ (0.142 kW/m$^2$×2), and the travel speed of the web was 70 m/min.

The web was transferred to two web transportation conveyers, thereafter transferred to a yankee dryer heated to 120° C., and dried.

Then, high-pressure steam was sprayed on the web using a steam nozzle. In this case, the pressure of the high-pressure steam was 0.7 MPa, its temperature was about 175° C., a distance between the bore of the steam nozzle and the upper surface of the web was 2.0 mm, the bore diameter of the steam nozzle was 500 μm, a bore pitch was 2.0 mm, and the travel speed of the web was 70 m/min. Further, suction force at which a suction drum sucked the web was −1 kPa. A 18-mesh perforated sleeve made of stainless steel was used on the outer periphery of the suction drum.

Then, the web was transferred to the yankee dryer, dried, and wound up to produce a nonwoven fabric.

Figure 8A:
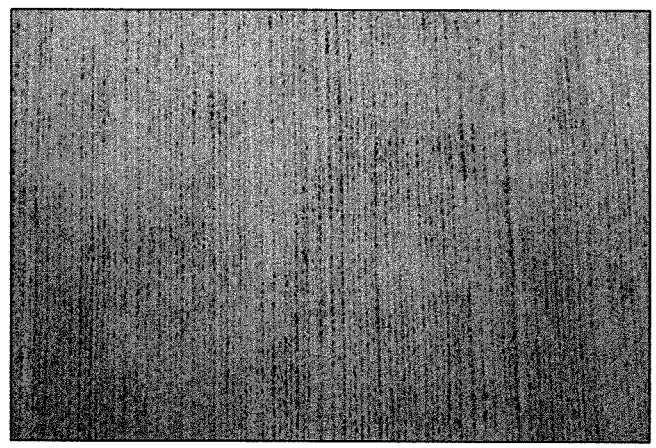
FIG. 8A represents a planar photograph of the water stream-sprayed surface of a web sprayed with water streams in Example 1.
Figure 8B:
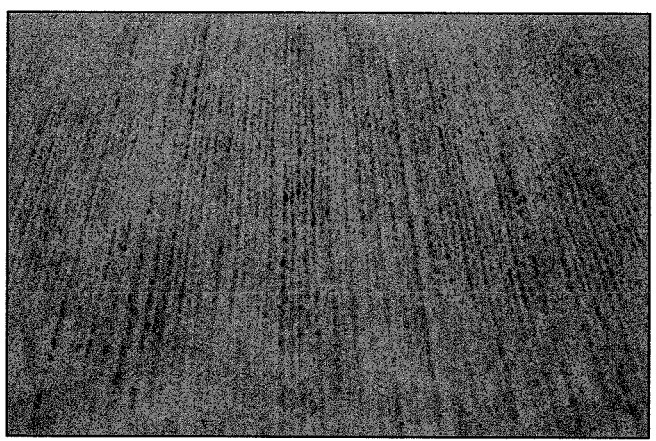
FIG. 8B represents an oblique photograph of the water stream-sprayed surface of a web sprayed with water streams in Example 1.

The photographs of the water stream-sprayed surface of the web sprayed with the water streams (photographed after drying) are represented in FIGS. 8A and 8B. FIG. 8A is a planar photograph; and FIG. 8B is an oblique photograph.

Figure 9A:
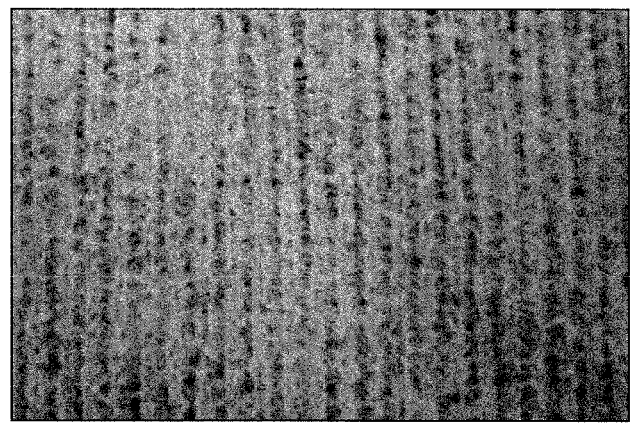
FIG. 9A represents a planar photograph of the steam-sprayed surface of a nonwoven fabric obtained in Example 1.
Figure 9B:
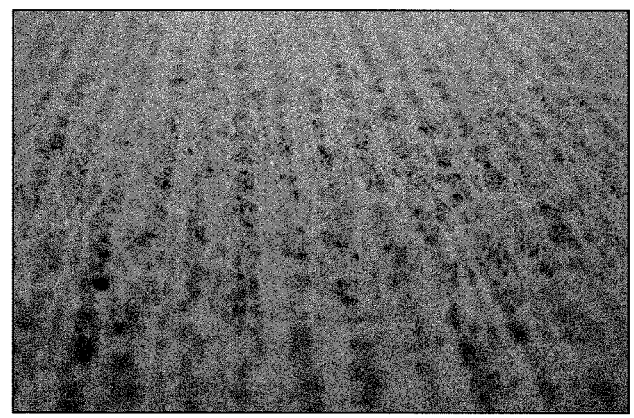
FIG. 9B represents an oblique photograph of the steam-sprayed surface of a nonwoven fabric obtained in Example 1.

The photographs of the steam-sprayed surface of the obtained nonwoven fabric (sprayed with steam and dried) are represented in FIGS. 9A and 9B. FIG. 9A is a planar photograph; and FIG. 9B is an oblique photograph.

Figure 10:
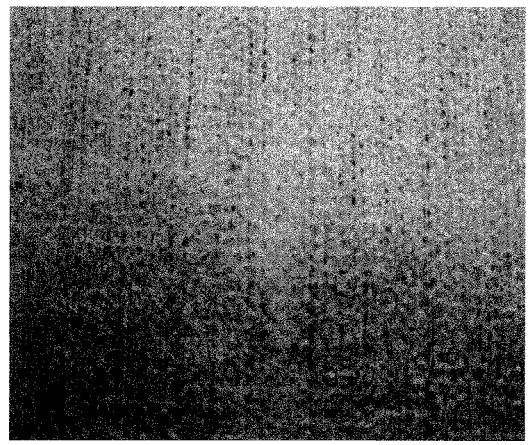
FIG. 10 is a photograph of the water stream-sprayed surface of the nonwoven fabric obtained in Example 1.

The planar photograph of the water stream-sprayed surface of the obtained nonwoven fabric is represented in FIG. 10.

The nonwoven fabric mass per unit area, the dry thickness, the density, the surface layer apparent density, the dry tensile strength, the dry tensile elongation, the wet tensile strength, and the wet tensile elongation of the obtained nonwoven fabric were measured. The measurement results are listed in Table 1.

The obtained nonwoven fabric was cut into 150 mm in width and 200 mm in length and impregnated with distilled water amounting to three times the dry mass of the nonwoven fabric to make a wet wipe.

An artificial fouling wiping-off property test was conducted using the made wet wipe to measure fouling removal ratios on the high-pressure water stream-sprayed surface and the high-pressure steam-sprayed surface, respectively. The measurement results are listed in Table 1.

Example 2

A nonwoven fabric was produced in the same conditions as in Example 1, except that web moisture content prior to spraying high-pressure steam was 10%, and a wet wipe was made and evaluated. The measurement results are listed in Table 1.

The web moisture content of 10% is the minimum moisture content at which fibers are raised and steam-sprayed line marks are applied in high-pressure steam spraying treatment;

and the moisture content of less than 10% makes hydrogen bonding strength between the fibers strong to preclude movement of the fibers.

Example 3

A nonwoven fabric was produced in the same conditions as in Example 1 except that a high-pressure steam spraying pressure was adjusted to a minimum of 0.3 MPa at which fibers are raised and steam-sprayed line marks are applied, and a wet wipe was made and evaluated. The measurement results are listed in Table 1.

Comparative Example 1

A nonwoven fabric was produced in the same conditions as in Example 1 except that high-pressure steam spraying treatment was not performed, and a wet wipe was made and evaluated. The measurement results are listed in Table 1.

A wiping-off property can be developed to some extent due to an effect of scraping away minute water stream-sprayed line marks by spraying high-pressure water streams; however, since fibers are not raised, it is difficult to enhance the wiping-off property because of a small contact area and small concavities and convexities.

Comparative Example 2

A nonwoven fabric was produced in the same conditions as in Example 1 except that high-pressure steam spraying treatment of a web that had not been subjected to high-pressure water stream spraying treatment was performed, and a wet wipe was made and evaluated. The measurement results are listed in Table 1.

A shape with concavities and convexities is easily applied to the web since water stream spraying treatment is not performed; however, fibers are weakly entangled, so that, when the fibers are going to be raised, they are excessively disentangled which results in falling-off of the fibers and it is difficult to make the fibers raised. Further, although it is bulky in appearance since the fibers are not raised, a contact area is reduced and a wiping-off property is not good.

Comparative Example 3

A nonwoven fabric was produced in the same conditions as in Example 1 except that a steam spraying pressure is adjusted to be a low pressure of 0.2 MPa at which fibers are inhibited from being raised, and a wet wipe was made and evaluated. The measurement results are listed in Table 1.

When the steam spraying pressure is low, a force for disentangling the fibers is low and it is difficult to raise the fibers.

TABLE 1

| | | Example 1 | Example 2 | Example 3 | Comparative Example 1 | Comparative Example 2 | Comparative Example 3 |
|---|---|---|---|---|---|---|---|
| NBKP | | 70% | 70% | 70% | 70% | 70% | 70% |
| Rayon | | 30% | 30% | 30% | 30% | 30% | 30% |
| Amount of energy (KW/m$^2$) of high-pressure water stream | | 0.284 | 0.284 | 0.284 | 0.284 | — | 0.284 |
| Steam-sprayed surface | | Surface opposite to water stream-sprayed surface | Surface opposite to water stream-sprayed surface | Surface opposite to water stream-sprayed surface | — | — | Surface opposite to water stream-sprayed surface |
| Steam spraying pressure (MPa) | | 0.7 | 0.7 | 0.3 | — | 0.7 | 0.2 |
| Temperature (° C.) of steam spray nozzle | | 210 | 210 | 210 | — | 210 | 210 |
| Bore diameter (μm) of steam spray nozzle | | 500 | 500 | 500 | — | 500 | 500 |
| Pitch (mm) of steam spray nozzle | | 2 | 2 | 2 | — | 2 | 2 |
| Number (lines) of lines of steam nozzles | | 2 | 2 | 2 | — | 2 | 2 |
| Gap distance (mm) between steam nozzlez and web | | 2 | 2 | 2 | — | 2 | 2 |
| Suction pressure (kPa) in steam spraying portion | | −5.0 | −5.0 | −5.0 | — | −5.0 | −5.0 |
| Specification (meshes) of substrate of steam spraying portion | | 18 | 18 | 18 | — | 18 | 18 |
| Web moisture content prior to spraying steam | | 45% | 10% | 45% | — | 45% | 45% |
| Nonwoven fabric mass per unit area | g/m$^2$ | 50.8 | 50.5 | 50.0 | 49.7 | 50.2 | 50.1 |
| Dry thickness | mm | 0.63 | 0.54 | 0.54 | 0.33 | 0.73 | 0.40 |
| Density | g/cm$^3$ | 0.08 | 0.09 | 0.09 | 0.15 | 0.07 | 0.13 |
| Surface layer apparent density (g/cm$^3$) | Water stream-sprayed surface | 0.16 | 0.17 | 0.17 | — | — | 0.15 |
| | Steam-sprayed surface | 0.033 | 0.069 | 0.072 | — | — | 0.12 |
| Dry tensile strength (N/25 mm) | MD | 14.5 | 15.2 | 10.8 | 15.6 | 7.6 | 15.9 |
| | CD | 9.7 | 10.4 | 4.9 | 11.1 | 3.1 | 4.1 |
| Dry tensile elongation (%) | MD | 3.7 | 3.8 | 4.2 | 2.9 | 3.3 | 4.1 |
| | CD | 16.7 | 13.1 | 11.4 | 13.1 | 16.8 | 10.5 |
| Wet tensile strength (N/25 mm) | MD | 2.8 | 3.6 | 2.8 | 3.8 | 1.5 | 3.1 |
| | CD | 2.1 | 2.0 | 2.5 | 2.4 | 0.7 | 2.5 |
| Wet tensile elongation (%) | MD | 24.3 | 25.9 | 21.2 | 28.9 | 30.8 | 31.2 |
| | CD | 33.1 | 38.8 | 36.1 | 40.6 | 37.4 | 42.3 |
| Fouling removal ratio (%) | Steam-sprayed surface | 11.1 | 7.5 | 7.0 | — | 4.3 | 5.5 |
| | Water stream-sprayed surface | 5.5 | 5.4 | 5.5 | 5.3 | — | 5.4 |

A web moisture content prior to spraying steam, a web moisture content after spraying steam, a web moisture content during winding, a web mass per unit area, a dry thickness, a density, a surface layer apparent density, a dry tensile strength, a dry tensile elongation, a wet tensile strength, a wet tensile elongation, and a fouling removal ratio were measured as described below.

[Web Moisture Content Prior to Spraying Steam]

A web dried by the dryer drum 20 is sampled in a size of 30 cm×30 cm, the outlet mass ($W_1$) of the dryer drum 20 is measured, and the sample piece is then left at rest in a constant-temperature bath at 105° C. for 1 hour and absolutely dried, followed by measuring its mass ($D_1$). Web moisture content (%) prior to spraying steam is calculated according to the following expression. The web moisture content prior to spraying steam is the mean value of ten measurement values.

$$\text{Web moisture content (\%) prior to spraying steam} = (W_1 - D_1)/W_1 \times 100$$

[Web Moisture Content after Spraying Steam]

A web sprayed with high-pressure steam from the steam nozzle 14 on one suction drum 15 is sampled in a size of 30 cm×30 cm, its mass ($W_2$) after passing through the steam nozzle 14 is measured, and the sample piece is then left at rest in a constant-temperature bath at 105° C. for 1 hour and absolutely dried, followed by measuring its mass ($D_2$). The web moisture content (%) after spraying steam is calculated according to the following expression. The web moisture content after spraying steam is the mean value of ten measurement values.

$$\text{Web moisture content (\%) after spraying steam} = (W_2 - D_2)/W_2 \times 100$$

[Web Moisture Content During Winding]

A web passing through the dryer drum 22 and wound up is sampled in a size of 30 cm×30 cm, its mass ($W_3$) after the winding is measured, and the sample piece is then left at rest in a constant-temperature bath at 105° C. for 1 hour and absolutely dried, followed by measuring its mass ($D_3$). The web moisture content (%) during winding is calculated according to the following expression. The web moisture content during winding is the mean value of ten measurement values.

$$\text{Web moisture content (\%) during winding} = (W_3 - D_3)/W_3 \times 100$$

[Nonwoven Fabric Mass Per Unit Area]

A nonwoven fabric mass per unit area was calculated by dividing the mass $D_3$ (g) of the sample absolutely dried when the web moisture content during winding was measured, by its area (0.09 m$^2$). The nonwoven fabric mass per unit area is the mean value of ten measurement values.

[Dry Thickness]

The thickness of the produced nonwoven fabric was measured on the measurement condition of a measuring load of 3 gf/cm$^2$ using a thickness gauge (manufactured by Daiei Kagaku Seiki Mfg. Co. Ltd., Model: FS-60DS) including a gauge head of 15 cm$^2$. The thicknesses of three places in one sample for measurement were measured and the mean value of the thicknesses of the three places was regarded as a dry thickness prior to pressing.

[Density]

A dry bulk density after pressing was calculated from the web mass per unit area and the dry thickness of the web after the above-mentioned pressing. The dry thickness of the web after the pressing was measured as described below. The web after the pressing was impregnated with liquid nitrogen, frozen, then cut with a razor, and returned to ordinary temperature, followed by measuring the thickness of the web after the pressing using an electron microscope (e.g., VE7800 from Keyence Corporation) at a magnification of 50 times. The reason why the absorbent article was frozen was because the thickness is prevented from being varied by compression during cutting with the razor. The density was calculated by dividing the mass per unit area of the web prior to the pressing by the thickness.

[Surface Layer Apparent Density]

The cross section of the nonwoven fabric was macrophotographed at a magnification of 50 times or more by a microscope or the like, the number of fibers per unit area of $t_A$ or $t_B$ in depth×0.5 mm in width was measured, and the weight of the fibers was calculated from the result to calculate the apparent density.

[Dry Tensile Strength]

Strip-shaped test pieces having a width of 25 mm, of which the longitudinal direction is the machine direction of the web, and strip-shaped test pieces having a width of 25 mm, of which the longitudinal direction is the cross direction of the web, were cut from the produced nonwoven fabric to make samples for measurement. The tensile strengths of the samples for measurement in the machine and cross directions, which samples were each three, were measured using a tensile testing machine (manufactured by Shimadzu Corporation, Autograph, Model: AGS-1kNG) including a load cell having a maximum load capacity of 50 N on the conditions of a grip distance of 100 mm and a tension speed of 100 mm/min. The mean value of the tensile strengths of the samples for measurement in the machine and cross directions, which samples were each three, was regarded as a dry tensile strength in the machine and cross directions.

[Dry Tensile Elongation]

Strip-shaped test pieces having a width of 25 mm, of which the longitudinal direction is the machine direction of the web, and strip-shaped test pieces having a width of 25 mm, of which the longitudinal direction is the cross direction of the web, were cut from the produced nonwoven fabric to make samples for measurement. The tensile elongations of the samples for measurement in the machine and cross directions, which samples were each three, were measured using the tensile testing machine (manufactured by Shimadzu Corporation, Autograph, Model: AGS-1kNG) including the load cell having a maximum load capacity of 50 N on the conditions of a grip distance of 100 mm and a tension speed of 100 mm/min. A tensile elongation is a value obtained by dividing a maximum elongation (mm) when a sample for measurement is pulled by the tensile testing machine, by a grip distance (100 mm). The mean value of the tensile elongations of the samples for measurement in the machine and cross directions, which samples were each three, was regarded as a dry tensile elongation in the machine and cross directions.

[Wet Tensile Strength]

Strip-shaped test pieces having a width of 25 mm, of which the longitudinal direction is the machine direction of the web, and strip-shaped test pieces having a width of 25 mm, of which the longitudinal direction is the cross direction of the web, were cut from the produced nonwoven fabric to make samples for measurement, and the samples for measurement were impregnated with water amounting to 2.5 times the mass of the samples for measurement (water content of 250%). The tensile strengths of the samples for measurement in the machine and cross directions, which samples were each three, were measured using the tensile testing machine (manufactured by Shimadzu Corporation, Autograph, Model: AGS-1kNG) including the load cell having a maximum load capacity of 50 N on the conditions of a grip distance of 100 mm and a tension speed of 100 mm/min. The mean value of the tensile strengths of the samples for measurement in the machine and cross directions, which samples were each three, was regarded as a wet tensile strength in the machine and cross directions.

[Wet Tensile Elongation]

Strip-shaped test pieces having a width of 25 mm, of which the longitudinal direction is the machine direction of the web, and strip-shaped test pieces having a width of 25 mm, of which the longitudinal direction is the cross direction of the web, were cut from the produced nonwoven fabric to make samples for measurement, and the samples for measurement were impregnated with water amounting to 2.5 times the mass of the samples for measurement (water content of 250%). The tensile elongations of the samples for measurement in the machine and cross directions, which samples were each three, were measured using the tensile testing machine (manufactured by Shimadzu Corporation, Autograph, Model: AGS-1kNG) including the load cell having a maximum load capacity of 50 N on the conditions of a grip distance of 100 mm and a tension speed of 100 mm/min. The mean value of the tensile elongations of the samples for measurement in the machine and cross directions, which samples were each three, was regarded as a wet tensile elongation in the machine and cross directions.

[Fouling Removal Ratio]

As simulated fouling, a paste of 12.6% by weight of carbon black, 20.8% by weight of beef tallow highly hydrogenated oil, and 66.6% by weight of liquid paraffin is prepared. The paste is mixed with hexane at a ratio (mass ratio) of 85:15. Onto a glass plate, 0.05 mL of hexane-diluted paste is dropped. After drying for 24 hours in a room at high temperature and high humidity (20° C., humidity of 60%), its color is scanned by a scanner. A wiping-off test (once) is conducted by a friction coefficient measuring apparatus from Tester Sangyo Co., Ltd. on the conditions of 150 mm/min and a load of 60 g. After the test, a change in color is scanned by the scanner and a rate of change in the color of an area of 16.9 mm×16.9 mm in a scanned area is calculated according to the following expression and regarded as a fouling removal ratio.

Fouling removal ratio (%)=$(C_0-C_1)/C_0\times 100$ wherein $C_0$ is a color prior to wiping off; and $C_1$ is a color after wiping off.

A greater color removal ratio can be considered to mean that more fouling can be removed. The measurement is performed for N=3, and the mean value of three measurements is regarded as a fouling removal ratio.

Some embodiments of the present invention are also defined by way of the following non-limiting features C1 to C13, J1 to J13, and U1 to U11, which are not specific to the detailed embodiments described above.

C1. A wet wipe comprising a nonwoven fabric impregnated with a liquid, wherein
a surface layer in a first surface of the nonwoven fabric has an apparent density of 0.030-0.10 g/cm$^3$ in a dry state;
a surface layer in a second surface of the nonwoven fabric has an apparent density of 0.12-0.20 g/cm$^3$ in a dry state; and
fibers are raised on at least the surface having a lower apparent density.

C2. The wet wipe according to C1, wherein
the fibers raised on the surface having a lower apparent density form a plurality of first ridges extending in parallel in a first direction; and
first grooves are formed between adjacent first ridges.

C3. The wet wipe according to C2, wherein
a plurality of second ridges extending in a second direction which is same as the first direction, and second grooves between adjacent second ridges are formed on the surface having a higher apparent density.

C4. The wet wipe according to C3, wherein
a distance between a top of the first ridge and a bottom of the first groove is greater than a distance between a top of the second ridge and a bottom of the second groove.

C5. The wet wipe according to C3 or C4, wherein
spacing between adjacent first ridges is greater than a spacing between adjacent second ridges.

C6. The wet wipe according to C3, wherein
the spacing between adjacent first ridges is 1.0-3.0 mm; and
the spacing between adjacent second ridges is 0.3-1.0 mm.

C7. The wet wipe according to C3, wherein
a distance between a top of the first ridge and a bottom of the first groove is 0.15-0.60 mm; and
a distance between a top of the second ridge and a bottom of the second groove is 0.05-0.10 mm.

C8. The wet wipe according to C1, wherein
30% or more of fibers constituting the nonwoven fabric are absorbable fibers.

C9. The wet wipe according to C1, wherein
the absorbable fibers comprise cellulose.

C10. The wet wipe according to C1, wherein
the fibers constituting the nonwoven fabric have fiber lengths of 20 mm or less.

C11. The wet wipe according to C1, wherein
the raised fibers are formed by spraying steam.

C12. The wet wipe according to C3, wherein
the first ridges and the first grooves are formed by spraying steam; and
the second ridges and the second grooves are formed by spraying a water stream.

C13. A method for manufacturing the wet wipe according to C1, comprising the steps of
supplying a mixture of fibers with water onto a substrate to form a web containing water on the substrate;
spraying a water stream onto the web from water stream nozzles placed in a cross direction of the web at equal spacings to entangle the fibers;
spraying steam on a surface opposite to the surface, on which the water stream is sprayed, of the web, on which the water stream is sprayed, from steam nozzles placed in the cross direction of the web at wider spaces than the spaces of the water stream nozzles, to raise fibers to obtain a nonwoven fabric of which the apparent densities of the front and back surfaces are different; and
impregnating the obtained nonwoven fabric with a liquid.

J1. A wet wipe comprising a nonwoven fabric impregnated with a liquid, wherein
a surface layer in a first surface of the nonwoven fabric has an apparent density of 0.030-0.10 g/cm$^3$ in a dry state;
a surface layer in a second surface of the nonwoven fabric has an apparent density of 0.12-0.20 g/cm$^3$ in a dry state; and
fibers are raised on at least the surface having a lower apparent density.

J2. The wet wipe according to J1, wherein
the fibers raised on the surface having a lower apparent density form a large number of first ridges extending in parallel in an identical direction; and
a first groove is formed between the two adjacent first ridges.

J3. The wet wipe according to J2, wherein
a large number of second ridges extending in a direction identical to those of the first ridges, and second grooves are formed on the surface having a higher apparent density.

J4. The wet wipe according to J3, wherein
a distance between a top of the first ridge and a bottom of the first groove is greater than a distance between a top of the second ridge and a bottom of the second groove.

J5. The wet wipe according to J3 or J4, wherein
a spacing between the two adjacent first ridges is greater than a spacing between the two adjacent second ridges.

J6. The wet wipe according to any one of J3 to J5, wherein
the spacing between the two adjacent first ridges is 1.0-3.0 mm; and
the spacing between the two adjacent second ridges is 0.3-1.0 mm.

J7. The wet wipe according to any one of J3 to J6, wherein
a distance between the top of the first ridge and the bottom of the first groove is 0.15-0.60 mm; and
a distance between the top of the second ridge and the bottom of the second groove is 0.05-0.10 mm.

J8. The wet wipe according to any one of J1 to J7, wherein
30% or more of fibers constituting the nonwoven fabric are absorbable fibers.

J9. The wet wipe according to any one of J1 to J8, wherein
the absorbable fibers comprise cellulose.

J10. The wet wipe according to any one of J1 to J9, wherein
the fibers constituting the nonwoven fabric have fiber lengths of 20 mm or less.

J11. The wet wipe according to any one of J1 to J10, wherein
the raised fibers are formed by spraying steam to blow weakly entangled fibers together.

J12. The wet wipe according to any one of J3 to J11, wherein
the first ridges and the first grooves are formed by spraying steam; and
the second ridges and the second grooves are formed by spraying a water stream.

J13. A method for manufacturing the wet wipe according to J1, comprising the steps of
supplying a mixture of fibers with water onto a substrate to form a web containing water on the substrate;
spraying a water stream on the web from water stream nozzles placed in a cross direction of the web at equal spacings to entangle the fibers;
spraying steam on a surface opposite to the surface, on which the water stream is sprayed, of the web, on which the water stream is sprayed, from steam nozzles placed in the cross direction of the web at wider spacings than the spacings of the water stream nozzles, to raise fibers to obtain a nonwoven fabric of which the apparent densities of the front and back surfaces are different; and
impregnating the obtained nonwoven fabric with a liquid.

U1. A wet wipe, comprising a nonwoven fabric impregnated with a liquid, wherein
a surface layer in a first surface of the nonwoven fabric has an apparent density of 0.030-0.10 g/cm$^3$ in a dry state;
a surface layer in a second surface of the nonwoven fabric has an apparent density of 0.12-0.20 g/cm$^3$ in a dry state; and
fibers constituting the nonwoven fabric are raised on at least the first surface.

U2. The wet wipe according to U1, wherein
the fibers raised on the first surface form a plurality of first ridges extending in parallel in an elongation direction; and
a plurality of first grooves each formed between two adjacent first ridges.

U3. The wet wipe according to U2, wherein
a plurality of second ridges extending in the elongation direction and second grooves are formed on the second surface.

U4. The wet wipe according to U3, wherein
a distance between a top of the first ridge and a bottom of the first groove is greater than a distance between a top of the second ridge and a bottom of the second groove.

U5. The wet wipe according to U3, wherein
a spacing between two adjacent first ridges is greater than a spacing between two adjacent second ridges.

U6. The wet wipe according to U3, wherein
the spacing between the two adjacent first ridges is 1.0-3.0 mm; and
the spacing between the two adjacent second ridges is 0.3-1.0 mm.

U7. The wet wipe according to U3, wherein
a distance between the top of the first ridge and the bottom of the first groove is 0.15-0.60 mm; and
a distance between the top of the second ridge and the bottom of the second groove is 0.05-0.10 mm.

U8. The wet wipe according to U1, wherein
30% or more of the fibers constituting the nonwoven fabric are absorbable fibers.

U9. The wet wipe according to U1, wherein
the absorbable fibers comprise cellulose.

U10. The wet wipe according to U1, wherein
the fibers constituting the nonwoven fabric have fiber lengths of 20 mm or less.

U11. A method for manufacturing a wet wipe comprising a nonwoven fabric impregnated with a liquid, wherein
a surface layer in a first surface of the nonwoven fabric has an apparent density of 0.030-0.10 g/cm$^3$ in a dry state;
a surface layer in a second surface of the nonwoven fabric has an apparent density of 0.12-0.20 g/cm$^3$ in a dry state; and
fibers constituting the nonwoven fabric are raised on at least the first surface,
the method comprising:
supplying a mixture of fibers with water onto a substrate to form a web containing water on the substrate;
spraying a water stream onto a surface of the web from water stream nozzles placed in a cross direction of the web at equal spacings to entangle the fibers;
spraying steam or a mixture of steam with another gas onto an opposite surface of the web from steam nozzles placed in the cross direction of the web at wider spacings than the spacings of the water stream nozzles, to raise the fibers to obtain the nonwoven fabric with the different apparent densities on the first and second surfaces; and
impregnating the obtained nonwoven fabric with the liquid.

This application claims the benefit of Japanese Application No. 2011-215072, the entire disclosure of which is incorporated by reference herein.

INDUSTRIAL APPLICABILITY

The wet wipe according to at least one embodiment of the present invention can preferably be used, e.g., for wiping the buttocks.

REFERENCE SIGNS LIST

1 Wet wipe
2 Nonwoven fabric
3 First ridge
4 First groove
5 Second ridge
6 Second groove
10 Nonwoven fabric manufacturing apparatus
11 Raw material supply head
12 Water stream nozzle
13 Suction box
14 Steam nozzle
15 Suction drum
16 Web formation conveyer
17 Suction pick up
18, 19 Web transportation conveyer
20, 21 Dryer drum
22 Wind-up machine
30 Web
31 High-pressure water stream
32 Groove
41 Mesh-like outer peripheral surface substrate of suction drum
51 High-pressure steam
52 Groove
54 Outer peripheral surface of suction drum

The invention claimed is:

1. A fibrous wet wipe, comprising a nonwoven fabric impregnated with a liquid, wherein
a surface layer in a first surface of the nonwoven fabric has an apparent density of 0.030-0.10 g/cm$^3$ in a dry state;
a surface layer in a second surface of the nonwoven fabric has an apparent density of 0.12-0.20 g/cm$^3$ in a dry state; and
fibers constituting the nonwoven fabric are raised on at least the first surface.

2. The wet wipe according to claim 1, wherein
the fibers raised on the first surface form a plurality of first ridges extending in parallel in a direction; and
the wet wipe further comprises, on the first surface, a plurality of first grooves each formed between two adjacent first ridges.

3. The wet wipe according to claim 2, wherein
a plurality of second ridges extending in the direction and second grooves are formed on the second surface.

4. The wet wipe according to claim 3, wherein
a distance between a top of the first ridge and a bottom of the first groove is greater than a distance between a top of the second ridge and a bottom of the second groove.

5. The wet wipe according to claim 3, wherein
a spacing between two adjacent first ridges is greater than a spacing between two adjacent second ridges.

6. The wet wipe according to claim 3, wherein
the spacing between the two adjacent first ridges is 1.0-3.0 mm; and
the spacing between the two adjacent second ridges is 0.3-1.0 mm.

7. The wet wipe according to claim 3, wherein
a distance between the top of the first ridge and the bottom of the first groove is 0.15-0.60 mm; and
a distance between the top of the second ridge and the bottom of the second groove is 0.05-0.10 mm.

8. The wet wipe according to claim 1, wherein
30% or more of the fibers constituting the nonwoven fabric are absorbable fibers.

9. The wet wipe according to claim 1, wherein
the absorbable fibers comprise cellulose.

10. The wet wipe according to claim 1, wherein
the fibers constituting the nonwoven fabric have fiber lengths of 20 mm or less.

11. A method of manufacturing a fibrous wet wipe comprising a nonwoven fabric impregnated with a liquid, wherein
a surface layer in a first surface of the nonwoven fabric has an apparent density of 0.030-0.10 g/cm$^3$ in a dry state;
a surface layer in a second surface of the nonwoven fabric has an apparent density of 0.12-0.20 g/cm$^3$ in a dry state; and
fibers constituting the nonwoven fabric are raised on at least the first surface, the method comprising:
supplying a mixture of fibers with water onto a substrate to form a web containing water on the substrate;
spraying a water stream onto a surface of the web from water stream nozzles placed in a cross direction of the web at equal spacings to entangle the fibers;
spraying steam or a mixture of steam with another gas onto an opposite surface of the web from steam nozzles placed in the cross direction of the web at wider spacings than the spacings of the water stream nozzles, to raise the fibers to obtain the nonwoven fabric with the different apparent densities on the first and second surfaces; and
impregnating the obtained nonwoven fabric with the liquid.

* * * * *